United States Patent [19]
Li et al.

[11] Patent Number: 5,744,029
[45] Date of Patent: Apr. 28, 1998

[54] GAS CHROMATOGRAPHY OVEN

[75] Inventors: Kenneth L. Li, Piedmont; Roger C. Tong, Berkeley, both of Calif.

[73] Assignee: Varian Associates, Inc., Palo Alto, Calif.

[21] Appl. No.: 792,016

[22] Filed: Feb. 3, 1997

[51] Int. Cl.$^6$ .................................................. B01D 15/08
[52] U.S. Cl. ...................... 210/198.2; 210/656; 210/175; 95/87; 96/101; 432/199
[58] Field of Search .................................. 210/656, 175, 210/180, 179, 198.2; 96/101, 102, 103; 95/87; 73/23.25; 432/199

[56] References Cited

U.S. PATENT DOCUMENTS

| | | | |
|---|---|---|---|
| 3,165,147 | 1/1965 | Roof | 96/102 |
| 3,305,000 | 2/1967 | Bullen | 96/102 |
| 3,841,059 | 10/1974 | McCabe | 96/102 |
| 4,038,055 | 7/1977 | Varano | 96/102 |
| 4,181,613 | 1/1980 | Welsh | 210/198.2 |
| 4,420,679 | 12/1983 | Howe | 219/400 |
| 4,599,169 | 7/1986 | Ray | 210/198.2 |
| 4,869,876 | 9/1989 | Arfman | 96/102 |
| 4,948,389 | 8/1990 | Klein | 95/87 |
| 5,032,151 | 7/1991 | Klein | 96/102 |
| 5,656,170 | 8/1997 | Henderson | 210/656 |

*Primary Examiner*—Ernest G. Therkorn

[57] ABSTRACT

A chromatography oven is described to achieve faster cool-down rates and to preferably lower the temperature difference that can be maintained between the oven temperature and ambient temperature. The oven includes a suitable housing having front and rear walls and four side walls, a fan within the housing adjacent to the rear walls, an ambient air intake vent means in the rear wall, and an exhaust vent means within a rear corner of one of the side walls adjacent to the rear wall for exhausting the tangential flow of air created by the rotating fan.

28 Claims, 6 Drawing Sheets

GAS CHROMATOGRAPHY OVEN

FIELD OF THE INVENTION

The invention relates generally to gas chromatography, and more particularly to an improvement in a gas chromatography oven to achieve more rapid cool-down rates.

BACKGROUND OF THE INVENTION

The current state of the art relating to gas chromatograph ovens is represented by the ovens disclosed and claimed in Welsh, U.S. Pat. No. 4,050,911, issued Sep. 27, 1977 and Welsh, U.S. Pat. No. 4,181,613, issued Jan. 1, 1980. Each of the ovens of this prior art include a rectangular oven housing having a front, rear and four side walls to form an enclosure to house chromatographic columns, a heating element and a motor driven fan. The fan is designed to mix air in the enclosure to minimize the temperature gradients that could degrade chromatographic analysis being performed in the columns (i.e. peak-splitting). Minimizing column temperature gradients are especially important in capillary gas chromatography. Ambient air is drawn through a first air passage in the oven door in the front of the housing and a plurality of air ducts on each side of the door by the fan in the oven of the '911 patent. The air is allowed to free flow through a second air passage in the sides of the enclosure. This design permits the lower pressure air region in the oven to draw the ambient air and the higher pressure air region to exhaust hot air from the oven.

Welsh noted in the '613 patent that prior oven designs, i.e. of the type disclosed in the '911 patent, directed the ambient air through the portion of the oven occupied by the chromatographic columns. Welsh pointed out the disadvantage of such a design was that columns were often subjected to unwanted temperature gradients caused by the flow of ambient air over the columns depending on their size and configuration. The improved oven design of the '613 patent places the ambient air intake port and the exhaust port on the rear wall of the enclosure. Specifically in reference to FIGS. 5–7 of the '613 patent, ambient air is drawn through intake port 72 in the rear wall adjacent fan shaft 70 where the air pressure is the lowest and exhausts through exhaust port 77 at a corner of the rear where the air pressure is the highest.

SUMMARY OF THE INVENTION

In accordance with the present invention, additional improvements have been made over the prior art gas chromatography ovens to achieve faster cool-down rates and preferably to lower the temperature difference that can be maintained between the oven temperature and ambient temperature. The chromatography oven of the present invention includes a suitable housing having front and rear walls and four side walls, i.e. a top side wall, a bottom side wall, a right side wall and a left side wall; a fan within the housing adjacent to the rear wall and having a longitudinal axis substantially parallel to the side walls; an ambient air intake vent means in the rear wall adjacent to the longitudinal axis; and an exhaust vent means within a rear corner of one of the side walls adjacent to the rear wall for exhausting the tangential flow of air created by the rotating fan.

Preferably, the intake vent means is offset a finite distance above the longitudinal axis of the fan. This allows substantially all of the incoming ambient air to traverse substantially the entire circumferential path of rotation of the fan, and to achieve maximum cool-down performance. The optimum performance is achieved with the air intake off center from the center of the fan axis of rotation which prevents the incoming air from "short circuiting" to the exhaust vent. The air becomes short circuited when the air that enters the oven is thrown out the exhaust vent without traversing the working area of the oven.

If the circumferential path of rotation of the fan is counterclockwise and the intake vent means is above the fan's longitudinal axis, the exhaust vent is positioned on one of the following rear corners of the four side walls of the oven of the present invention: the right rear corner of top side wall, the top rear corner of left side wall, the left rear corner of bottom side wall, and the bottom rear corner of right side wall. Similarly, if the circumferential path of rotation of the fan is clockwise, the exhaust vent is positioned on one of the following rear corners: the left rear corner of top side wall, the top rear corner of right side wall, the right rear corner of bottom side wall, and the bottom rear corner of left side wall.

In one embodiment of the chromatograph oven of the present invention, the ambient air intake vent means includes the intake vent and a plenum chamber on the rear wall having an inlet, an outlet in alignment with the intake vent and a door covering the inlet. The advantage of this embodiment is that the door covering the inlet to the intake vent is in the same plane as a door that covers the exhaust vent. This permits the control of the opening and closing of these doors during operation by a single motor and connecting arm as described in more detail below.

BRIEF DESCRIPTION OF THE DRAWINGS

FIG. 3 is a top view of the oven of the embodiment shown in FIG. 2;

FIG. 4 is a front view, partial broken away, of the oven of another embodiment of the present invention;

FIG. 5 is a partial side view of the oven of the embodiment shown in FIG. 4;

DESCRIPTION OF THE PREFERRED EMBODIMENTS

Figure 1:
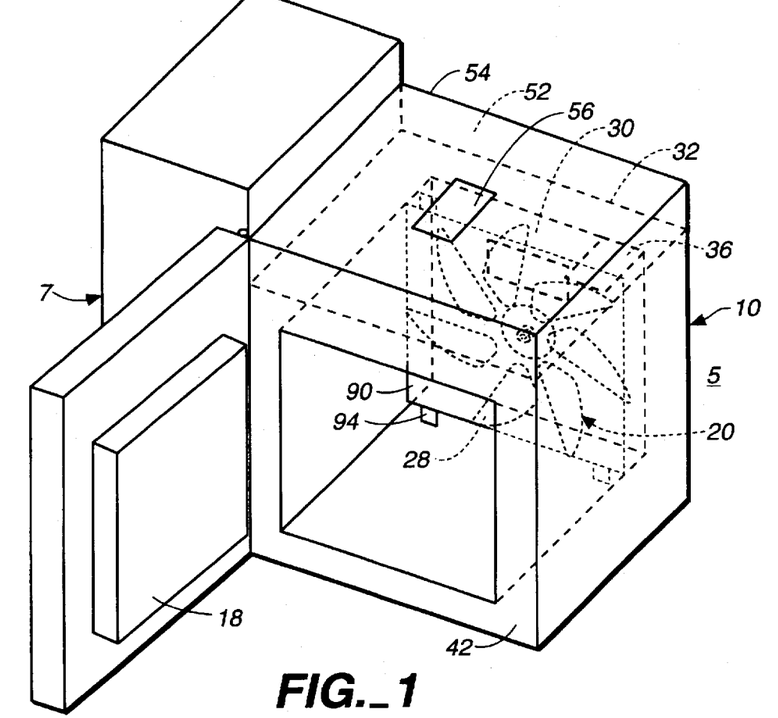
FIG. 1 is a perspective view of one embodiment of a chromatographic unit including the oven of the present invention.
Figure 2:
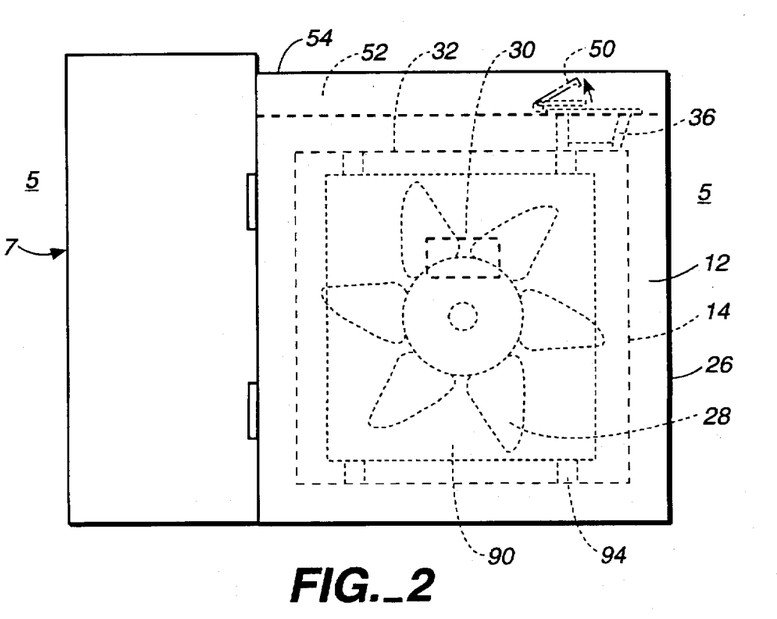
FIG. 2 is a front view of the embodiment shown in FIG. 1.
Figure 6:
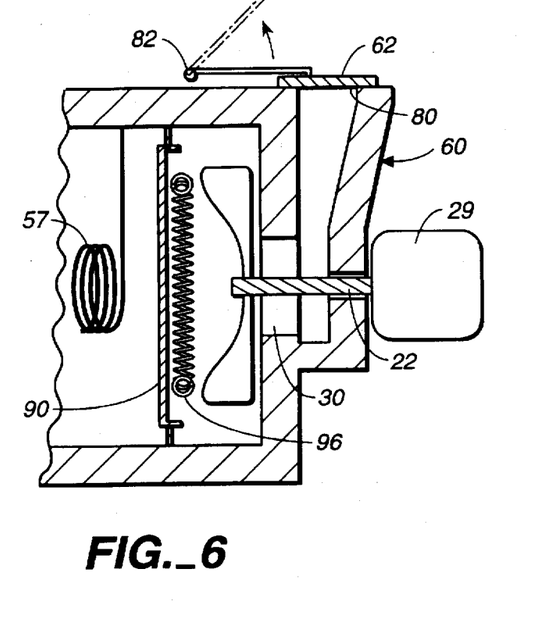
FIG. 6 is a partial cross-sectional view taken along line 6—6 of FIG. 4.
Figure 7:
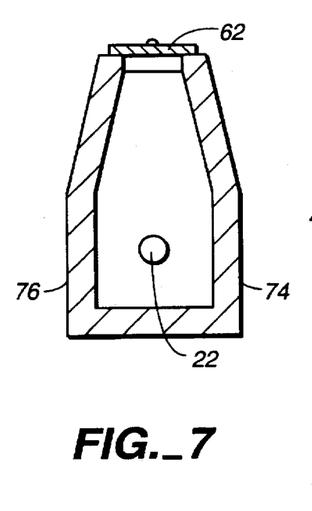
FIG. 7 is a partial cross-sectional view taken along line 7—7 of FIG. 5.

Referring now to FIGS. 1–3, there is shown chromatographic unit 5 consisting of sub-unit 7 comprising the control electronics, pneumatics and detector electronics and a preferred embodiment of the present invention, chromatograph oven 10. Thermal insulation layer 12 of a heat resistant material forms a sandwich between inner and outer faces of each of the six walls 14 which form oven 10. Preferably walls 14 form a substantially cubic interior to achieve the optimum air flow patterns while minimizing the surface area for a given interior volume. Fan 20 is mounted on rotatable shaft 22 extending through rear wall 24 and parallel to right side wall 26 and left side wall 27. Fan 20 is shown substantially in the center of rear wall 24 with blades 28 for rotation in a counterclockwise direction by means of motor 29. Alternatively, blades 28 can be oriented for rotation in a clockwise direction if the location of intake vent 30 and exhaust vent 36 are maintained as described below Ambient air intake vent 30 is positioned on rear wall 24. Intake vent 30 is shown in this embodiment offset a short distance, e.g. about one inch, toward top side wall 32 of oven 10 from the longitudinal axis of shaft 22. Intake vent 30 in the embodiment shown in FIGS. 4–6 is concentric with shaft 22 of fan 20.

Figure 9:
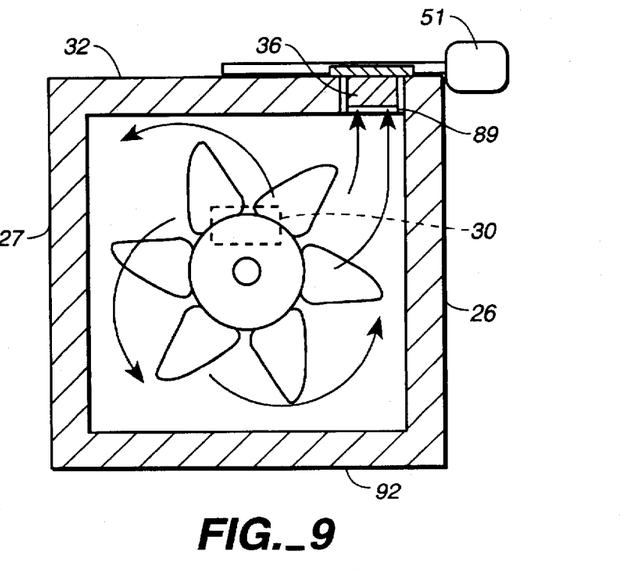
FIG. 9 is a cross-sectional view taken along line 9—9 of FIG. 5.

In the preferred embodiment shown in FIGS. 1–3, exhaust vent 36 is in the right rear corner of top side wall 32 relative to front wall 42. Exhaust vent 36 is critically positioned to tangentially face the oncoming rotational flow of air created by fan 20 as shown in FIG. 9. Exhaust vent 36 has door 50 operated by motor 51. In this preferred embodiment, vent 36 can also be positioned in left rear corner of top side wall 32 adjacent rear wall 24 when fan blades 28 are oriented for rotation in a clockwise direction. Alternately in another preferred embodiment of this invention, exhaust vent 36 can be positioned on either right side wall 26 or left side wall 27 depending on the rotation of the fan and the configuration of chromatographic unit. In the embodiment shown in FIGS. 1–3, the exhaust from vent 36 is directed through exhaust ducting (not shown) in space 52 between top side wall 32 and exterior top wall 54 and out the top of unit 5.

Top side wall 32 of oven 10 has means through which injectors and detectors (not shown) can be conveniently mounted. An injector is connected to the beginning of a chromatographic column 57 which is mounted within the column oven through door 18. The injectors provide a means for introducing a volume of sample compound and delivering the sample into the column in combination with a carrier gas. Compounds are separated by the chromatographic column; they pass out of the end of the column into the detectors which are used for sensing these compounds.

Exterior top 54 of chromatographic unit 5 has openings 56 for introducing samples into the injector device by suitable sample means such as the VARIAN 8200CX AutoSampler.

Space 58 between rear wall 24 and exterior rear wall 59 houses motor 29 for fan 20 and motor 51 which serves to operate door 50 on exhaust vent 36 and the door (not shown) on intake vent 30. Exterior rear wall 59 is partially perforated to allow ambient air to enter space 58 and intake vent 30. Rear wall 59 is easily removed for servicing fan 20 and motors 29 and 51.

The mechanism of cooling down a hot gas chromatography column oven involves not only effective convective heat transfer of the hot air within the oven, but also the heat capacity and thermal diffusivity of the oven walls and various elements within the oven, e.g., fan blade, heater elements, and baffling. The best mode of operation balances the need to have not only effective convective heat transfer in accordance with the oven of the present invention to drive the cooling, but also lowest practical heat storage within the oven, and to have elements of the oven designed, by geometry and/or material selection, for fast thermal responsiveness to temperature change which is related to the thermal diffusivity of the material.

Each of the elements within the column oven that is heated stores thermal energy that must be extracted during column oven cool-down. The stored thermal energy of any given element is a function of the element material heat capacity multiplied by its mass and the change in temperature during cool down. The elements exposed most closely to the internal air of the column oven are most heavily weighted since they are heated to the highest temperature and are most closely thermally coupled with air which is to be cooled down. Optimization of oven design begins with minimizing thermal mass of these oven elements, either by reducing size or thickness of elements.

The interior faces of the prior art oven walls have been typically made from stainless steel, a material which is resistant to the high operating temperatures often encountered in gas chromatography, with thickness typically at least about 0.016 in. Such thickness is well suited to conventional punch-press/shearing manufacturing methods. By use of newer manufacturing methods, such as laser cutting or photo-chemical etching, the use of much thinner material, e.g., 0.010 in. thick stainless steel, can be economically used, reducing the thermal mass of the interior faces of the oven walls to approximately 50% of the prior art oven designs, while maintaining adequate component strength.

The prior art oven shown in FIG. 2 of Welsh, U.S. Pat. No. 4,181,613, which embodiment is shown in FIG. 5, includes an internal rear wall 66 of the oven cavity, in addition to the usual interior wall 64. This internal rear wall 66 of the oven cavity shown in FIG. 2 of Welsh constitutes roughly 15% additional surface area associated with sheet stainless steel components, when compared with an oven of the preferred embodiment of this invention. Coupled with the roughly 50% reduction in thickness, the heat capacity of the oven sheet metal can be reduced to less than 50% of this prior art oven design.

Further reductions in heat capacity were explored by investigating engineering materials other than stainless steel. Titanium sheet holds approximately 60% of the energy that is held in stainless steel of the same thickness, and has similar strength. Oxidation of titanium was found to be acceptably low in a prototype operated at about 450° C. Titanium has a thermal diffusivity approximately 1.6 times that of stainless steel; this indicates that titanium would give off its heat energy at a faster rate when exposed to similar cooling means. A single-piece part for the interior faces could be manufactured out of vitreous carbon/graphite, which has very low density and heat capacity, and high thermal diffusivity. Parts can be manufactured by molding a hydrocarbon polymer, then carbonizing at a high temperature. For applications limited to about 400° C., aluminum sheet could be an economical and readily available alternative to stainless steel sheet for interior walls of the column oven. Aluminum has a very low density and heat capacity, and very high conductivity, resulting in very high thermal diffusivity. Aluminum is preferably limited to applications under 250° C. due to softening and loss of strength at elevated temperatures. Anodizing may be desirable for controlled protection against oxidation.

Thermal insulation layer 12, having a thickness ranging from about ½ to about 3 inches, preferably about 1 inch to about 1½ inches, is between the inner and outer faces of walls 14. The outer face or skin consists of a metal, e.g.

aluminum or steel, or a high temperature plastic, typically having a thickness of about 1/16 inch. An air gap is maintained between this outer skin and the outer structural panels of walls 14. The air gaps serve to insure that safe surface temperatures are maintained on the exterior surfaces of oven 10 that could contact the user. The air gaps also serve to prevent damage to the electronics and pneumatics housed within sub-unit 7. An industrial standard is to maintain the exterior surface temperatures of all equipment not to exceed about 70° C. The depth of the air gap ranges from about 1/2 to about 1 1/2 inches for right and left side walls 26 and 27, front wall 42, including door 18, and bottom side wall 92. Top side wall 32 and rear wall 24 are separated from the user by exterior top wall 54 and exterior rear wall 59 and the air gaps of spaces 52 and 58 are considerably greater than 1 1/2 inches to accommodate motors 29 and 51, vent door 50 and other equipment.

Figure 8:
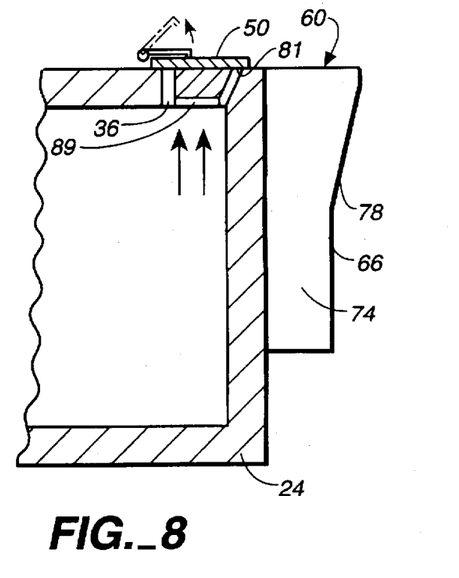
FIG. 8 is a partial cross-sectional view taken along line 8—8 of FIG. 4.

FIGS. 4–9 illustrate another embodiment of the present invention as well as the remaining internals of a typical chromatograph oven. The numbering for FIGS. 4–9 is the same as in FIGS. 1–3 for all elements common to both sets of figures. The only basic difference between the embodiment shown in FIGS. 103 and that shown in FIGS. 4–9 is the use of plenum chamber 60 to place door 62 controlling air to intake vent 30 on the same plane as door 50 of exhaust vent 36. Consequently, FIGS. 4 and 6 serve to show the front and side views of the internal elements for both embodiments. In the embodiment shown in FIGS. 4–9, ambient air enters intake vent 30 adjacent rotatable shaft 22 of fan 20 through plenum chamber 60. Plenum chamber 60 is mounted on the outside of rear wall 24 so its thermal mass is decoupled from oven 10. This minimizes any increase in the thermal time constant of oven 10. Plenum chamber 60 as shown in FIGS. 5, 6 and 8 has a depth from plenum wall 66 to rear wall 24 and a width from plenum side wall 74 to plenum side wall 76. The depth adjacent intake vent 30 is less than the depth from sloping wall 78 to rear wall 24. This minimizes the length of shaft 22 passing through this section of plenum chamber 40 and through the center of intake vent 30. The depth of wall 78 to rear wall 24 adjacent inlet opening 80 is at a maximum to accommodate the size of inlet opening 80. The aspect ratio, which in this case is the width divided by the depth ranges from approximately two (2) adjacent intake vent 30 to approximately one (1) adjacent inlet opening 80 where shaft 22 does not interfere with incoming ambient air. These features of maintaining the aspect ratio near to unity, and the cross-sectional area of chamber 60 roughly constant avoids excessive blocking of the flow of ambient air.

By placing intake opening 80 and exhaust vent 36 on the same plane external oven 10, opening and closing intake vents 30 and exhaust vent 36 can easily be done using insulated swing doors 50 and 62 each mounted on the same actuating shaft 82 using motor 51.

The asymmetrical location of exhaust vent 36 in one of the four corners of oven 10 will disturb the symmetry of the recirculating flow of air. The symmetry is especially disturbed when exhaust vent 36 is open. Even when vent 36 is closed, the fact that door 50 is separated from interior wall 32 by about 1/2 to 3 inches, preferably about 1 to 1 1/2 inch, of insulation, a pocket is created by the vent opening through the thickness of the insulation. This pocket generates a turbulent eddy flow within itself to result in an asymmetrical temperature gradient in that corner of oven 10. Air shield 89 (shown in FIGS. 8 and 9) parallel to exhaust vent door 50 maintains relatively equal pressure and flow symmetry in the four rear corners of oven 10. When vent door 50 is closed, shield 89 is coplanar to top side wall 32 and will block the bulk of the turbulent eddy flow from entering the exhaust vent opening between top side wall 32 and exterior top wall 54 of oven 10. As exhaust vent 36 begins to open, air shield 89 rotates with door 50. In the fully open position, sufficient space exists around door 50 and air shield 89 to permit free passage of exhaust air from oven 10 to exhaust ducting.

The internal elements common to each of the embodiments of gas chromatography oven 10 of the present invention include baffle 90, with integral protective screen in the center portion, attached between top side wall 32 and bottom side wall 92 by fasteners 94 and heater coil 96 between fan 20 and baffle 90. Baffles are used to constrain the flow from the fan to enhance the pressure gradient across the vents.

Figure 12A:
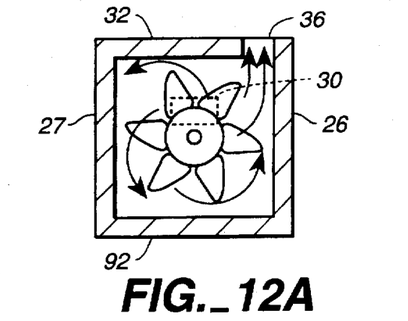
FIG. 12A–12D illustrate the four intake vent locations and the four rear corner locations for the exhaust vent in one of the side walls of the oven of the present invention when the circumferential path of rotation of the fan is counter-clockwise.
Figure 12B:
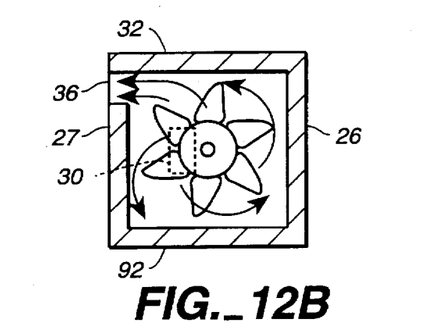
Figure 12C:
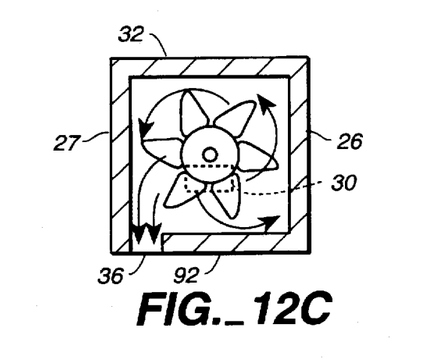
Figure 12D:
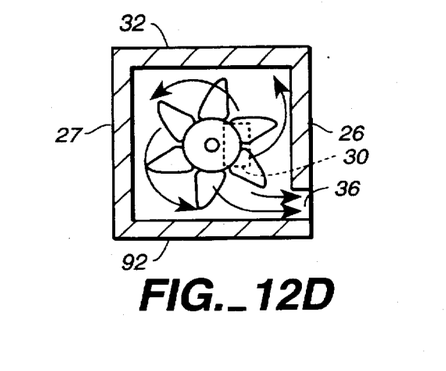
Figure 12E:
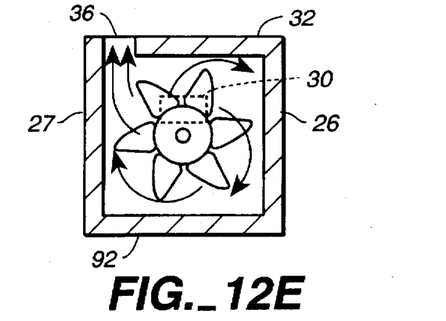
FIG. 12E–12H illustrate the four intake vent locations and the four rear corner locations for the exhaust vent in one of the side walls of the oven of the present invention when the circumferential path of rotation of the fan is clockwise.
Figure 12F:
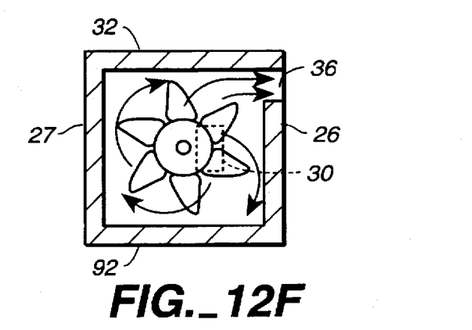
Figure 12G:
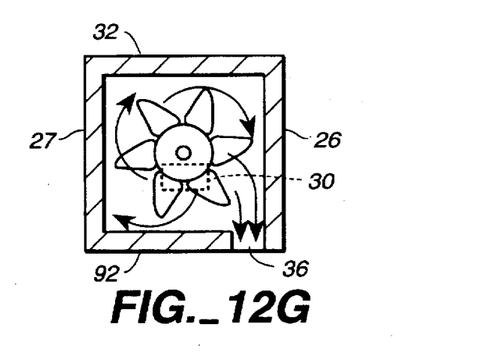
Figure 12H:
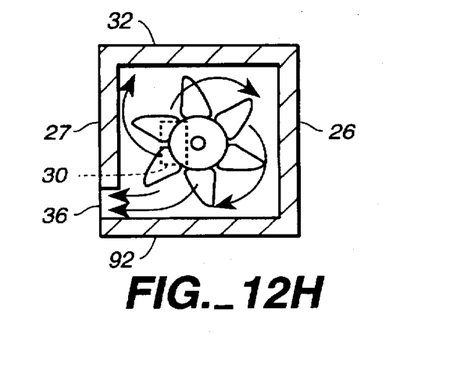

FIGS. 12A–12H illustrate the eight possible rear corner locations for the exhaust vent in one of the four side walls of the oven of the present invention depending on whether the circumferential path of rotation of the fan is counterclockwise or clockwise. FIG. 12A shows exhaust vent 36 on the right rear corner of top side wall 32. This is one of the most preferred locations of exhaust vent 36 as discussed above in connection with FIGS. 1–3. FIG. 12B shows exhaust vent 36 on the top rear corner of left side wall 27; FIG. 12C shows exhaust vent 36 on the left rear corner of bottom side wall 92; and FIG. 12D shows exhaust vent 36 on the bottom rear corner of right side wall 26. In all of the four locations of the exhaust vent shown in FIGS. 12A–12D, the circumferential path of rotation is counterclockwise. FIG. 12E shows exhaust vent 36 on the left rear corner of top side wall 32. This is the other of the most preferred locations of exhaust vent 36. FIG. 12F shows exhaust vent 36 on the top rear corner of right side wall 26; FIG. 12G shows exhaust vent 36 on the right rear corner of bottom side wall 92; and FIG. 12H shows exhaust vent 36 on the bottom rear corner of left side wall 27. The circumferential path of rotation is clockwise for the rotational path of the fan shown in FIGS. 12E–12H.

Prototypes were constructed of an oven of substantially the same configuration as that described above in connection with FIGS. 1–3 as well as an oven in which the only difference was that the oven exhaust vent was placed in rear wall 24 in the manner described and claimed in Welsh, U.S. Pat. No. 4,181,613. These prototype ovens were evaluated in these experiments to determine their relative thermal response rates to heating at substantially constant power, and cooling with the fan and respective venting concepts. In order to ensure a repeatable measurement of relative thermal response, standard tests were defined for heating and cooling.

The starting conditions of these experiments required that the oven be substantially in thermal equilibrium. This was achieved by holding the oven at the starting condition, e.g., power input, temperature and the like, etc., for a sufficiently long time. Confirmation of thermal equilibrium was monitored by measuring the temperature on the external face of the oven wall insulation, and waiting until that location had substantially reached the same temperature as if a very long time, e.g., 24 hours, of time had passed. Real chromatographic analyses often require rapid temperature programming to save time. In actual practice, therefore, the column ovens are rarely in thermal equilibrium. Actual thermal response rates would be expected to be different than those achieved in these experiments. Relative rates of the comparative designs should still be roughly proportional, under similar conditions.

Figure 10A:
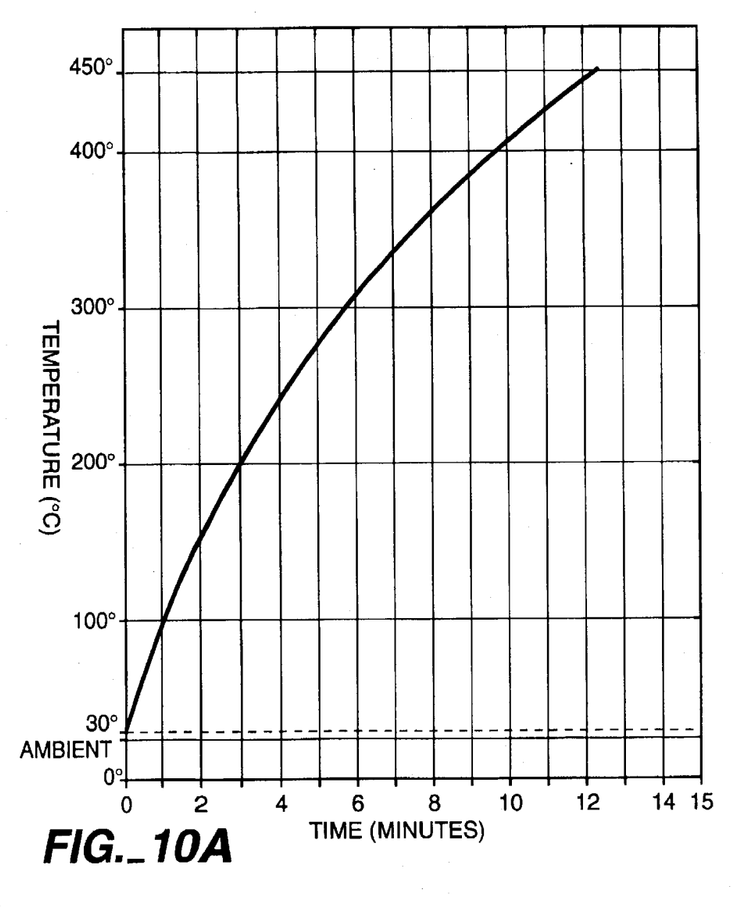
FIGS. 10A and 10B are of the oven temperature heat-up and cool-down of the oven of the present invention.
Figure 10B:
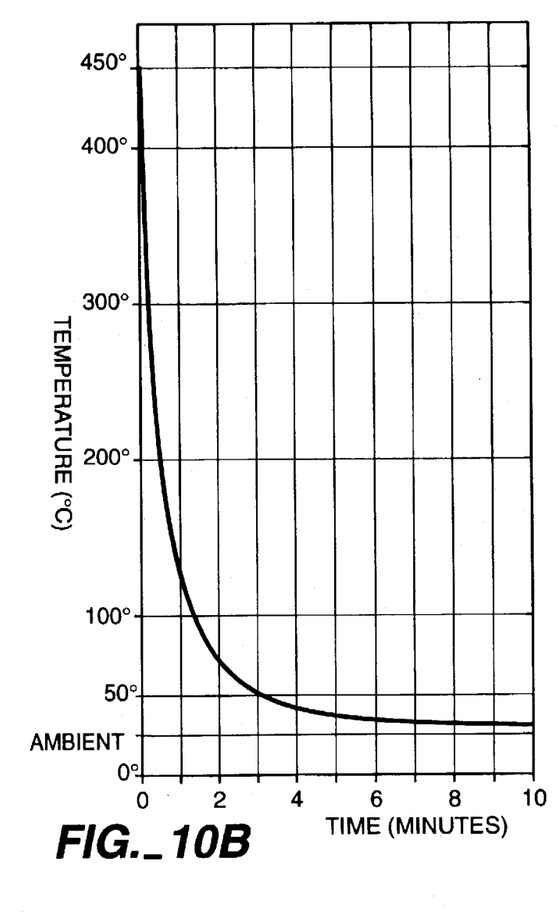
Figure 11A:
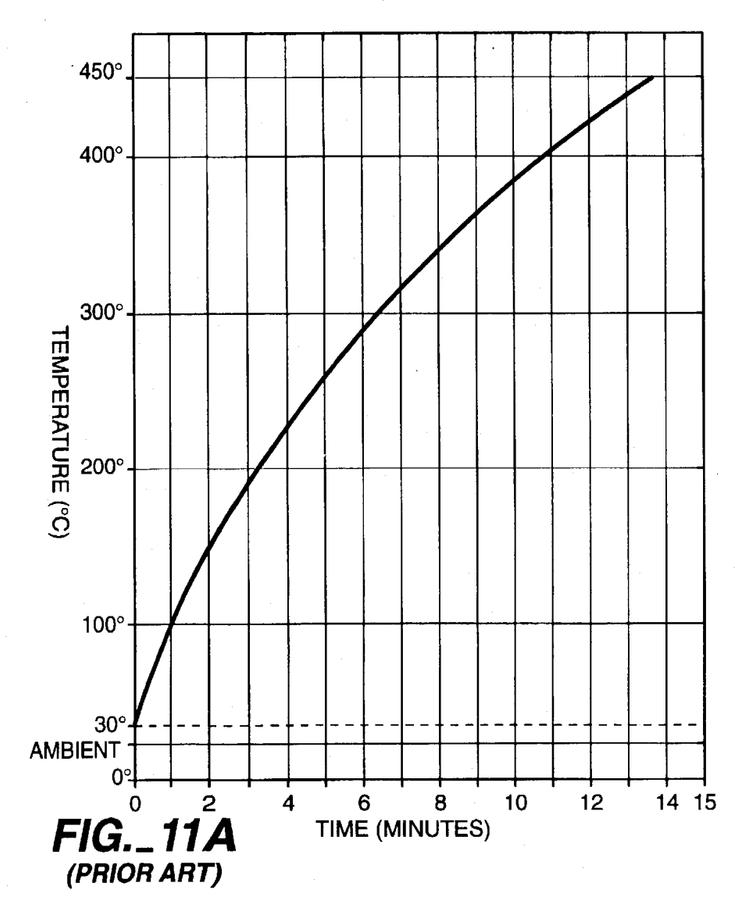
FIGS. 11A and 11B are of the oven temperature heat-up and cool-down of the oven of the prior art.
Figure 11B:
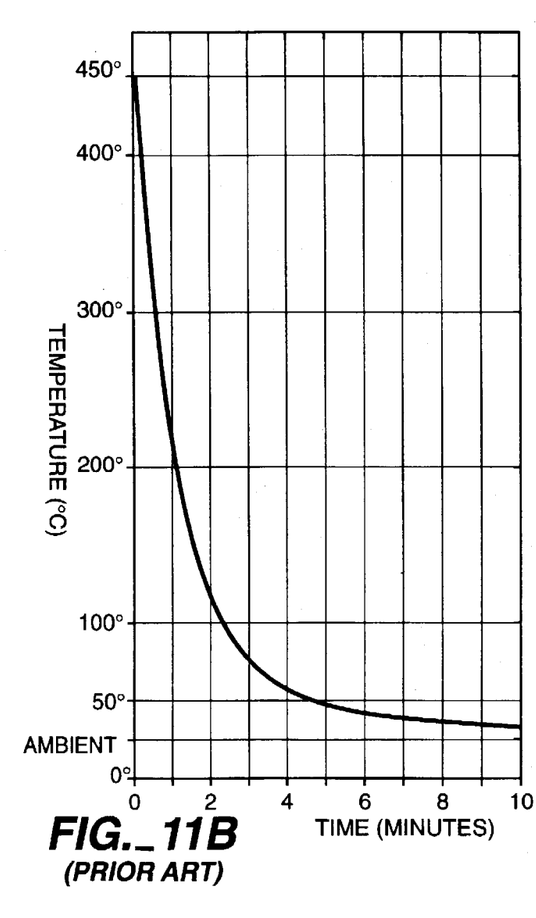

FIG. 10 shows the heat-up and cool-down performance of the oven in accordance with the present invention. FIG. 11 shows the heat-up and cool-down performance of the oven of the prior art. During heat-up, the oven of the present invention went from 30° C. to 450° C. in 12.3 minutes. This compares to a heat-up period of 13.7 minutes for the prior art oven. The oven was maintained at about 450° C. for a period of time to reach equilibrium before it was cooled down. During the cool-down, the oven went from 450° C. to 50° C. in 3.1 minutes compared to 4.6 minutes for the prior art oven. The cool-down period for the oven of the present invention is about two thirds of the cool-down period of the prior art oven.

CONCLUSION

The design logic underlying the invention in its several embodiments may be summarized in the following synopsis. Radial and axial pressure gradients are created by rotating fan blades. The placement of intake and exhaust ports and the sense of the internal air circulation should be regarded as related by the logic of propelling air along an initial airflow path which will sweep out the greatest volume of internal oven space. This is accomplished in the specific designs discussed above by supplying the intake ambient air along the initial airflow axis which is parallel to, but displaced from the fan rotation axis. The displacement promotes the spiral propagation of input air. The exhaust aperture is oriented to place the plane of that aperture orthogonal to the plane of the input aperture. Thus the intake and exhaust apertures are respectively axial and tangential with respect to the fan axis. The intake aperture, proximate the fan axis, is in a relatively low pressure zone. The exhaust aperture, relatively further from the fan axis, is in a relatively high pressure zone. The intake and exhaust axes are recognized to exhibit an angular separation about the fan axis. The sense of rotary air circulation about this fan axis is selected to maximize the angular path taken from the intake port to the exhaust port for the circulating air. In this manner, the cooling air efficiently displaces a large internal volume of the oven air and maximizes heat transfer by convection from internal oven surfaces. The increased efficiency provides a more direct thermal control of the oven interior. The more rapid thermal cooling (the usual desideratum) promotes other desired operating modes, such as rapid thermal stabilization.

Without departing from the spirit and scope of this invention, one of ordinary skill in the art can make various changes and modifications to the invention to adapt it to various usages and conditions. As such, these changes and modifications are properly, equitably, and intended to be, within the full range of equivalents of the following claims.

What is claimed is:

1. An oven comprising:
   a housing having a front wall, a rear wall, and four side walls;
   a fan mounted within said housing adjacent to said rear wall and having a longitudinal axis substantially parallel to said side walls;
   intake means comprising an ambient air intake vent in said rear wall; and
   exhaust means comprising an exhaust vent in a rear corner of one of said side walls and oriented to tangentially face the oncoming rotational flow of air created by said fan for exhausting the air.

2. The oven of claim 1 wherein said intake vent is positioned in said rear wall behind said fan and wherein a door is removably mounted to cover said intake vent.

3. The oven of claim 2 wherein said intake vent is offset from the longitudinal axis of said fan to allow substantially all of the incoming ambient air to traverse substantially the entire circumference of the rotational flow of air created by said fan, and to achieve maximum cool-down performance.

4. The oven of claim 2 wherein said four side walls comprises a top side wall, a bottom side wall, a right side wall and a left side wall.

5. The oven of claim 4 wherein the rotational flow of air is counterclockwise, wherein said exhaust vent is positioned in the right rear corner of said top side wall, and wherein said exhaust means also comprises a door removably mounted to cover said exhaust vent.

6. The oven of claim 4 wherein the rotational flow of air is clockwise, wherein said exhaust vent is positioned in the left rear corner of said top side wall, and wherein said exhaust means also comprises a door removably mounted to cover said exhaust vent.

7. The oven of claim 4 wherein the rotational flow of air is counterclockwise, wherein said exhaust vent is positioned in the top rear corner of said left side wall, and wherein said exhaust means also comprises a door removably mounted to cover said exhaust vent.

8. The oven of claim 4 wherein the rotational flow of air is clockwise, wherein said exhaust vent is positioned in the top rear corner of said right side wall, and wherein said exhaust means also comprises a door removably mounted to cover said exhaust vent.

9. The oven of claim 1 wherein said intake vent is positioned in said rear wall behind said fan and wherein said intake means also comprises a plenum chamber mounted on said rear wall and has an inlet distal to said intake vent.

10. The oven of claim 9 wherein said plenum chamber has a longitudinal axis transverse to the longitudinal axis of said fan and is positioned on an exterior surface of said rear wall.

11. The oven of claim 10 wherein a rotatable shaft passes through said plenum chamber and upon which said fan is mounted along the longitudinal axis of said shaft.

12. The oven of claim 9 wherein said inlet means also comprises an inlet door removably mounted on said plenum chamber to cover said inlet.

13. The oven of claim 12 wherein said exhaust means also comprises an exhaust door removably mounted to cover said exhaust vent.

14. The oven of claim 13 wherein an air shield is mounted parallel to said exhaust door, within the space between the interior and exterior surface of the wall and has an interior surface substantially coplanar with the interior surface of the wall.

15. The oven of claim 9 wherein said intake means also comprises an inlet door removably mounted on said plenum chamber to cover said inlet, wherein said exhaust means also comprises an exhaust door removably mounted on one of said side walls to cover said exhaust vent and wherein actuating means for opening and closing each door is operably connected to each of said doors.

16. The oven of claim 15 wherein an air shield is mounted parallel to said exhaust door, within the space between the interior and exterior surface of the wall and has an interior surface coplanar with the interior surface of the wall, and is opened with the exhaust door by said activating means.

17. A chromatograph oven comprising:
   a housing having an interior surface and an exterior surface having a front wall, a rear wall, a bottom side wall, a top side wall, and right and left side walls normal to said front and rear walls,
   a fan mounted within said interior surface of said housing adjacent to said rear wall and having a longitudinal axis substantially parallel to said right and left side walls, intake means comprising an ambient air intake vent in said rear wall, and exhaust means comprising an exhaust vent in a rear corner of one of said top, right and left side walls and oriented to tangentially face the oncoming rotational flow of air created by said fan for exhausting the air.

18. The oven of claim 17 wherein said intake vent is positioned in said rear wall behind said fan and wherein said intake means also comprises a plenum chamber mounted on said rear wall and has an inlet distal to said intake vent and an outlet aligned with said intake vent.

19. The oven of claim 18 wherein said plenum chamber has a longitudinal axis transverse to the longitudinal axis of said fan and is positioned on an exterior surface of said rear wall.

20. The oven of claim 19 wherein a rotatable shaft passes through said plenum chamber and upon which said fan is mounted along the longitudinal axis of said shaft.

21. The oven of claim 18 wherein said inlet means also comprises an inlet door removably mounted on said plenum chamber to cover said inlet.

22. The oven of claim 21 wherein said exhaust means also comprises an exhaust door removably mounted on one of said top, right and left side walls to cover said exhaust vent.

23. The oven of claim 22 wherein actuating means for opening and closing each door is operably connected to each of said doors.

24. The oven of claim 23 wherein a layer of insulation is between an interior surface and an exterior surface of each of said walls and wherein an air shield is mounted parallel to said exhaust door, within the space between the interior and exterior surface of the wall and has an interior surface coplanar with the interior surface of the wall, and is opened with the exhaust door by said activating means.

25. The oven of claim 22 wherein a layer of insulation is between said interior surface and exterior surface of said housing, and wherein an air shield is mounted parallel to said exhaust door, within the space between the interior and exterior surface of the wall and has an interior surface coplanar with the interior surface of the wall.

26. The oven of claim 17 wherein said intake vent is offset from the longitudinal axis of said fan to allow substantially all of the incoming ambient air to traverse substantially the entire circumference of the rotational flow of air created by said fan, and to achieve maximum cool-down performance.

27. The oven of claim 17 wherein the rotational flow of air is counterclockwise, wherein said exhaust vent is positioned in a right rear corner of said top side wall, and wherein said exhaust means also comprises a door removably mounted on said top side wall to cover said exhaust vent.

28. The oven of claim 17 wherein the rotational flow of air is clockwise, wherein said exhaust vent is positioned in a left rear corner of said top side wall, and wherein said exhaust means also comprises a door removably mounted on said top side wall to cover said exhaust vent.

* * * * *